US008815416B2

(12) United States Patent
Kai et al.

(10) Patent No.: US 8,815,416 B2
(45) Date of Patent: Aug. 26, 2014

(54) ORGANIC ELECTROLUMINESCENT DEVICE USING A BIPYRIMIDINE COMPOUND

(75) Inventors: Takahiro Kai, Kitakyushu (JP); Junya Ogawa, Kitakyushu (JP); Toshihiro Yamamoto, Kitakyushu (JP)

(73) Assignee: Nippon Steel & Sumikin Chemical Co., Ltd., Tokyo (JP)

( * ) Notice: Subject to any disclaimer, the term of this patent is extended or adjusted under 35 U.S.C. 154(b) by 275 days.

(21) Appl. No.: 12/746,260

(22) PCT Filed: Dec. 24, 2008

(86) PCT No.: PCT/JP2008/073468
§ 371 (c)(1),
(2), (4) Date: Jun. 4, 2010

(87) PCT Pub. No.: WO2009/084546
PCT Pub. Date: Jul. 9, 2009

(65) Prior Publication Data
US 2010/0244013 A1 Sep. 30, 2010

(30) Foreign Application Priority Data
Dec. 27, 2007 (JP) ................................. 2007-336283

(51) Int. Cl.
H01L 51/54 (2006.01)
C09K 11/06 (2006.01)

(52) U.S. Cl.
USPC ........... 428/690; 428/917; 313/504; 313/506; 257/40; 257/E51.026

(58) Field of Classification Search
None
See application file for complete search history.

(56) References Cited

U.S. PATENT DOCUMENTS

| | | | |
|---|---|---|---|
| 5,948,551 A | 9/1999 | Gompper et al. | |
| 2002/0034655 A1 | 3/2002 | Watanabe et al. | |
| 2003/0027016 A1* | 2/2003 | Ara et al. ...................... | 428/690 |
| 2003/0198831 A1 | 10/2003 | Oshiyama et al. | |
| 2006/0041126 A1* | 2/2006 | Schafer et al. ................. | 544/242 |
| 2006/0110622 A1* | 5/2006 | Uchida et al. .................. | 428/690 |
| 2006/0134460 A1* | 6/2006 | Kondakova et al. ........... | 428/690 |
| 2007/0018571 A1* | 1/2007 | Hwang et al. .................. | 313/504 |

FOREIGN PATENT DOCUMENTS

| | | |
|---|---|---|
| EP | 1486550 A1 | 12/2004 |
| JP | 2003-31368 A | 1/2003 |
| JP | 2004-31004 A | 1/2004 |
| JP | 2007-88015 A | 4/2007 |
| JP | 2007-99961 A | 4/2007 |
| WO | WO 2004/084824 A2 | 10/2004 |
| WO | WO 2008/117826 A1 | 2/2008 |

OTHER PUBLICATIONS

Inomata et al. "High-Efficiency Organic Electrophosphorescent Diodes Using 1,3,5-Triazine Electron Tranpsort Materials" Chem. Mater. 2004, 16, 1285-1291. Date of online publication: Mar. 3, 2004.*
Hughes et al. "Electron-transporting materials for organic electroluminescent and electrophosphorescent device" J. Mater. Chem. 2005, 15, 94-107. Date of online publication: Nov. 18, 2004.*
Son et al. "Blue Organic Electrophosphorescence Diodes using Diarylamino-substittued Heterocyclic Compounds as Host Material" J. Photopolym. Sci. Technol. 2007, 20, 47-51. Date of publication: Aug. 3, 2007.*
International Preliminary Report on Patentability mailed on Aug. 26, 2010, in connection with PCT International Application No. PCT/JP2008/073468.
Search Report issued Aug. 18, 2011, in European Patent Application No. 08867153.2.
Baxter et al., "Inorganic Arrays via Multicomponent Self-Assembly: The Spontaneous Generation of Ladder Architectures", Chemical Communications, No. 17, 1996, pp. 2019-2020.
Cai et al., "Solventless Synthesis of the 2,2'-Bipyrimidine Derivatives", Yingyong Huaxue, Chinese J. of Applied Chem. vol. 21, No. 1, 2004, pp. 107-108.
Crossley et al., "The Synthesis of Some Lipophilic Tetradentate Ligands for Use in the Formation of Metal-Linked Polymers", Australian Journal of Chemistry, vol. 47, No. 4., 1994, pp. 723-238.
Doh-Ura et al., "Chelating Compound, Chrysoidine, Is More Effective in Both Antiprion Activity and Brain Endothelial Permeability Than Quinacrine", Cellular and Molecular Neurobiology, vol. 27, No. 3, 2007, pp. 303-316.
Inagaki et al., "Synthesis of Pd Complexes Combined with Photosensitizing of a Ruthenium (II) Polypyridyl Moiety LThrough a Series of Substituted Bipyrimidine Bridges, Substituent Effect of the Bridging Ligand on the Photocatalytic Dimerization of α-Methylstyrene", Inorg.Chem. vol. 46,No. 7,2007 pp. 2432-2445.
Itami et al., "Pyrimidine-Core Extended π-Systems: General Synthesis and Interesting Fluorescent Properties", J. Amer. Chem. Soc., vol. 126, No. 47, 2004, p. 15396-15397.
Lafferty et al., "The Preparation and Properties of Certain Pyridylpyrimidines and Bidiazines as Potential Chelating Agents for Iron (II)", J. of Organic Chemistry, vol. 32, No. 5, 1967, pp. 1591-1596.
Michael D. Sevilla, "Electron Spin Resonance Study of Several Purine and Pyrimidine Radical Anions", J. Phys. Chem., vol. 74, No. 4, 1970, pp. 805-811.

(Continued)

Primary Examiner — Andrew K Bohaty
(74) Attorney, Agent, or Firm — Birch, Stewart, Kolasch & Birch, LLP

(57) ABSTRACT

Disclosed is an organic electroluminescent device (organic EL device) which is improved in luminous efficiency, fully secured of driving stability, and of simple constitution. Also disclosed is a compound useful for the fabrication of said organic electroluminescent device. This compound for organic electroluminescent device is a bipyrimidyl compound which has a basic skeleton of 2,2'-bipyrimidyl and is substituted by an aromatic hydrocarbon group, an aromatic heterocyclic group, or a substituted amino group. The aforementioned organic electroluminescent device has a light-emitting layer between an anode and a cathode which are piled one upon another on a substrate and the light-emitting layer contains a phosphorescent dopant and the aforementioned bipyrimidyl compound as a host material.

4 Claims, 1 Drawing Sheet

(56) References Cited

OTHER PUBLICATIONS

Nasielski et al., "Efficient Coupling of 2-Halopyrimidines to 2,2'-Bipyrimidines", Synthetic Communications, vol. 21, No. 7, 1991, pp. 901-906.

Nelson et al., "Cu, Ni, and Pd Mediated Homocoupling Reactions in Biaryl Syntheses: The Ullmann Reaction", Organic Reactions, vol. 63, 2004, pp. 264-285.

Riesgo et al., "Evaluation of Diimine Ligand Exchange on Cu(I)", Inorganic Chemistry, vol. 40, No. 11, 2001, pp. 2541-2546.

* cited by examiner

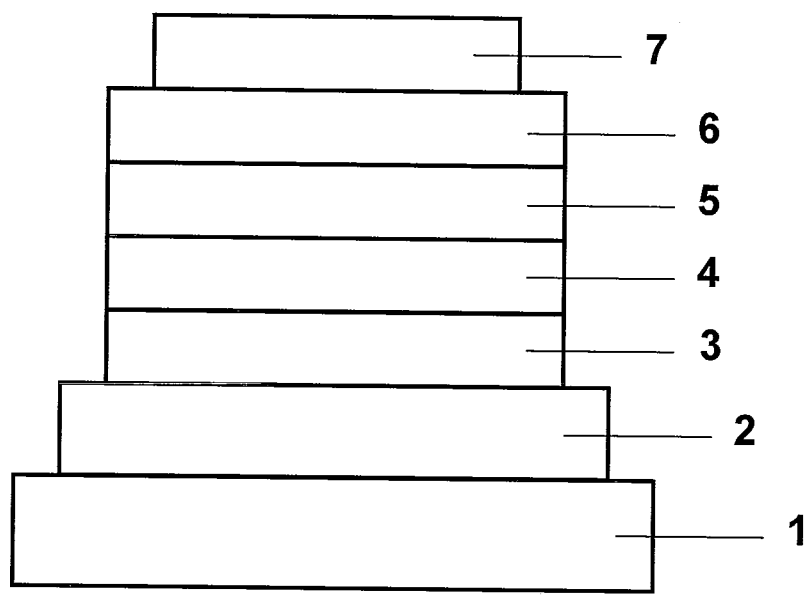

ORGANIC ELECTROLUMINESCENT DEVICE USING A BIPYRIMIDINE COMPOUND

FIELD OF TECHNOLOGY

This invention relates to a compound for organic electroluminescent device and to an organic electroluminescent device using the same and, more particularly, to a thin film device whose light-emitting layer composed of an organic compound emits light upon application of an electrical field.

BACKGROUND TECHNOLOGY

An organic electroluminescent device (hereinafter referred to as an organic EL device) in its simplest structure is generally constituted of a light-emitting layer sandwiched between a pair of counter electrodes and functions by utilizing the following phenomenon. Upon application of an electrical field between the electrodes, electrons are injected from the cathode and holes are injected from the anode and they recombine in the light-emitting layer with emission of light.

In recent years, organic thin films have been used in the development of organic EL devices. In particular, in order to enhance the luminous efficiency, the kind of electrodes has been optimized for the purpose of improving the efficiency of injecting carriers from the electrodes and a device has been developed in which a hole-transporting layer of an aromatic diamine and a light-emitting layer of 8-hydroxyquinoline aluminum complex (hereinafter referred to as Alq3) are disposed in thin film between the electrodes. This device has brought about a marked improvement in the luminous efficiency over the conventional devices utilizing single crystals of anthracene and the like and thereafter the developmental works of organic EL devices have been focused on commercial applications to high-performance flat panels featuring self-luminescence and high-speed response.

In another effort to enhance the luminous efficiency of the device, the use of phosphorescence in place of fluorescence is investigated. The aforementioned device containing a hole-transporting layer of an aromatic diamine and a light-emitting layer of Alq3 and many other devices utilize fluorescence. The use of phosphorescence, that is, emission of light from the excited triplet state is expected to enhance the luminous efficiency approximately three to four times that of the conventional devices utilizing fluorescence (emission of light from the excited singlet state). To achieve this objective, the use of coumarin derivatives and benzophenone derivatives in the light-emitting layer has been investigated, but these compounds merely produced luminance at an extremely low level. Thereafter, europium complexes were tried to utilize the excited triplet state, but failed to emit light at high efficiency. In recent years, as is mentioned in the patent document 1, a large number of researches are conducted with the objective of enhancing the luminous efficiency and extending the service life while mainly utilizing organic metal complexes such as iridium complexes.

Patent document 1: JP2003-515897 A
Patent document 2: JP2001-313178 A
Patent document 3: JP3711157 B
Patent document 4: JP2006-510732 A
Non-patent document 1: Applied Physics Letters, 2003, 83, 569-571
Non-patent document 2: Applied Physics Letters, 2003, 82, 2422-2424

A host material to be used together with the aforementioned dopant material becomes important in order to enhance the luminous efficiency. Of the host materials proposed thus far, a typical example is 4,4'-bis(9-carbazolyl)biphenyl (hereinafter referred to as CBP) which is a carbazole compound presented in the patent document 2. CBP exhibits relatively good luminous characteristics when used as a host material for green phosphorescent emitters, typically tris(2-phenylpyridine)iridium complex (hereinafter referred to as Ir(ppy)3). On the other hand, CBP fails to perform at sufficiently high luminous efficiency when used as a host material for blue phosphorescent emitters. This is because the energy level of the lowest triplet excited state of CBP is lower than that of common blue phosphorescent emitters and the triplet excitation energy of a blue phosphorescent emitter in use is transferred to CBP. That is to say, if a phosphorescent host material were designed to have triplet excitation energy higher than that of a phosphorescent emitter, the triplet excitation energy of the said phosphorescent emitter would be confined effectively and, as a result, the luminous efficiency would be enhanced. With the objective of improving this energy-confining effect, the triplet excitation energy is increased by modifying the structure of CBP in the non-patent document 1 and the luminous efficiency of bis[2-(4,6-difluorophenyl)pyridinato-N, C2']iridium picolinate (hereinafter referred to as FIrpic) is improved by this means. Similarly, the luminous efficiency is enhanced by using 1,3-dicarbazolylbenzene (hereinafter referred to as mCP) as a host material in the non-patent document 2. However, these host materials are not satisfactory in practical use, particularly from the viewpoint of durability.

Moreover, the host material needs to have balanced electrical charges (hole and electron) injection/transport properties in order to enhance the luminous efficiency. The electron transport property is inferior to the hole transport property in the case of CBP and this disturbs the balance of electrical charges in the light-emitting layer and causes excess holes to flow out to the side of the cathode thereby reducing the probability of recombination of holes and electrons in the light-emitting layer and decreasing the luminous efficiency. Furthermore, in the case where an electron-transporting material like Alq3 whose energy level of the lowest triplet excited state is lower than that of Ir(ppy)3 is used, there may also arise the possibility that the luminous efficiency decreases due to transfer of the triplet excitation energy from the dopant to the electron-transporting material.

One of the means to prevent holes from flowing out to the electron-transporting layer is to provide a hole-blocking layer between the light-emitting layer and the electron-transporting layer. This hole-blocking layer accumulates holes efficiently in the light-emitting layer and contributes to improve the probability of recombination of holes and electrons in the light-emitting layer and enhance the luminous efficiency (the patent document 2). Hole-blocking materials in general use include 2,9-dimethyl-4,7-diphenyl-1,10-phenanthroline (hereinafter referred to as BCP) and p-phenylphenolato-bis(2-methyl-8-quinolinolato)aluminum (hereinafter referred to as BAlq). These materials can prevent holes from flowing out of the light-emitting layer to the electron-transporting layer; however, the lowest energy level of the excited triplet state of both of them is lower than that of a phosphorescent dopant such as Ir(ppy)3 and sufficient luminous efficiency cannot be obtained.

Moreover, BCP tends to crystallize even at room temperature and lacks reliability as a hole-blocking material and the life of the device is extremely short. Although BAlq is reported to have a Tg of approximately 100° C. and provide the device with relatively good life, its hole-blocking ability is not enough.

The aforementioned examples indicate that, in order for an organic EL device to perform at high luminous efficiency, a host material is required to have high triplet excitation energy and to be balanced in the electrical charges (hole and electron) injection/transport properties. Furthermore, the host material is hopefully a compound furnished with good electrochemical stability, high heat resistance, and excellent stability in the amorphous state. However, no compound capable of satisfying these properties on a practical level has been known at the present time.

The patent documents 3 and 4 disclose some compounds having a specified pyrimidine skeleton for use in organic EL devices. However, the patent document 3 merely discloses compounds which contain two or more pyrimidine-2,6-diyl groups having a conjugated substituent at the p-position and a method for preparing them and, although the document contains a description to the effect that they are useful as materials for organic EL devices, it does not verify their usefulness as such. On the other hand, the patent document 4 discloses compounds which contain a pyrimidine skeleton and can be used as a material for the light-emitting layer, but it discloses no compounds containing a bipyrimidine skeleton nor their use as a phosphorescent host material.

DISCLOSURE OF THE INVENTION

Problems to be Solved by the Invention

In applications of organic EL devices to display devices such as flat panel displays, it is necessary to improve the luminous efficiency of the device and, at the same time, to fully secure the driving stability of the device. Under the aforementioned circumstances, an object of this invention is to provide an organic EL device which exhibits such high efficiency and good driving stability as to be practically useful and to provide a compound suitable therefor Means to Solve the Problems The inventors of this invention have found that the aforementioned problems can be solved by using a bipyrimidine compound of specified structure for an organic EL device and completed this invention.

That is, the inventors have found that a group of compounds having a bipyrimidine skeleton shows well-balanced electrical charges (hole and electron) injection/transport properties and clarified that organic EL devices containing the said compounds show excellent characteristics.

The inventors additionally found that the aforementioned group of compounds shows good stability when formed into thin film and good heat stability, clarified that organic EL devices containing the said compounds exhibit excellent driving stability and good durability, and completed this invention.

This invention relates to a compound for organic electroluminescent device which has a bipyrimidine skeleton represented by general formula (1):

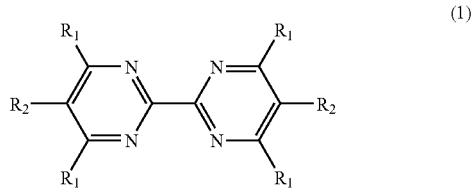

in the formula, $R_1$ is independently a hydrogen atom, an aromatic hydrocarbon group of 6 to 25 carbon atoms, an aromatic heterocyclic group of 2 to 24 carbon atoms, or an amino group substituted by an aromatic hydrocarbon group or aromatic heterocyclic group and $R_2$ is independently a hydrogen atom, an alkyl group of 1 to 12 carbon atoms, an alkoxyl group of 1 to 12 carbon atoms, or an amino group substituted by a hydrocarbon group or heterocyclic group.

Further, this invention relates to an organic electroluminescent device constituted of an anode, one or multiple organic layers, and a cathode piled one upon another on a substrate wherein the said organic layer or layers contain the aforementioned compound for organic electroluminescent device. From another point of view, this invention relates to an organic electroluminescent device constituted of an anode, one or multiple organic layers, and a cathode piled one upon another on a substrate wherein at least one of the organic layers is a light-emitting layer, the light-emitting layer contains a host material and a phosphorescent dopant, the content of the phosphorescent dopant in the light-emitting layer is 5 to 10 wt %, and the host material contains a compound for organic electroluminescent device represented by the aforementioned general formula (1).

Further, this invention can be expressed in the following modes.

1) The aforementioned compound for organic electroluminescent device wherein, in general formula (1), $R_1$ is independently an aromatic hydrocarbon group of 6 to 14 carbon atoms, an aromatic heterocyclic group of 3 to 13 carbon atoms, or an amino group substituted by an aromatic hydrocarbon group of 6 to 14 carbon atoms or aromatic heterocyclic group of 3 to 13 carbon atoms.

2) The aforementioned compound for organic electroluminescent device wherein, in general formula (1), $R_2$ is a hydrogen atom or an alkyl group of 1 to 12 carbon atoms.

3) The aforementioned compound for organic electroluminescent device wherein, in general formula (1), $R_1$ is a phenyl group or a phenyl group substituted by an alkyl group of 1 to 3 carbon atoms and $R_2$ is a hydrogen atom or an alkyl group of 1 to 3 carbon atoms.

4) The aforementioned organic electroluminescent device constituted by an anode, one or multiple organic layers, and a cathode piled one upon another on a substrate wherein the organic layer containing the aforementioned compound for organic electroluminescent device is at least one layer selected from the group of a light-emitting layer, a hole-transporting layer, an electron-transporting layer, and a hole-blocking layer.

5) The aforementioned organic electroluminescent device wherein the organic layer containing the aforementioned compound for organic electroluminescent device further contains a phosphorescent dopant.

BRIEF DESCRIPTION OF THE DRAWING

FIG. 1 schematically shows the cross section of an example of an organic EL device fabricated according to this invention.

Explanation of symbols: 1 substrate; 2 anode; 3 hole-injecting layer; 4 hole-transporting layer; 5 light-emitting layer; 6 electron-transporting layer; 7 cathode.

PREFERRED EMBODIMENTS OF THE INVENTION

A compound for organic electroluminescent device according to this invention is represented by the aforementioned general formula (1).

In general formula (1), $R_1$ is independently a hydrogen atom, an aromatic hydrocarbon group of 6 to 25 carbon atoms, an aromatic heterocyclic group of 2 to 24 carbon atoms, or an amino group substituted by an aromatic hydrocarbon group or aromatic heterocyclic group.

Of the aromatic hydrocarbon groups of 6 to 25 carbon atoms here, those of 6 to 14 carbon atoms are preferred. Of the aromatic heterocyclic groups of 2 to 24 carbon atoms, those of 3 to 13 carbon atoms are preferred. Of the amino groups substituted by an aromatic hydrocarbon group or aromatic heterocyclic group, those substituted by an aromatic hydrocarbon group of 6 to 14 carbon atoms or aromatic heterocyclic group of 3 to 13 carbon atoms are preferred.

In general formula (1), $R_2$ is independently a hydrogen atom, an alkyl group of 1 to 12 carbon atoms, an alkoxyl group of 1 to 12 carbon atoms, or an amino group substituted by a hydrocarbon group or heterocyclic group. A hydrogen atom and an alkyl group of 1 to 12 carbon atoms are preferred.

Here, the hydrocarbon groups as substituents for the amino group include alkyl groups of 1 to 12 carbon atoms and aromatic hydrocarbon groups of 6 to 25 carbon atoms, preferably 6 to 14 carbon atoms. The heterocyclic groups as substituents include aromatic heterocyclic groups of 3 to 13 carbon atoms.

In the case where $R_1$ or $R_2$ is an aromatic heterocyclic group, it is preferably an aromatic heterocyclic group containing 1 to 3 nitrogen atoms.

Preferable examples of the aromatic hydrocarbon groups include a phenyl group, a naphthyl group, a phenanthryl group, anthryl group, indenyl group, a biphenylyl group, a terphenylyl group, and tetraphenylyl group. More preferable are a phenyl group, a biphenylyl group, a terphenylyl group, and a naphthyl group.

Preferable examples of the aromatic heterocyclic groups include a thienyl group, a furyl group, a pyranyl group, a pyrrolyl group, an imidazolyl group, a pyrazolyl group, an isothiazolyl group, an isoxazolyl group, a pyridyl group, a pyrazinyl group, a pyrimidinyl group, a pyridazinyl group, a thianthrenyl group, an isobenzofuryl group, a chromenyl group, a xanthenyl group, a phenoxathinyl group, an indolidinyl group, an isoindolyl group, an indanzolyl group, a purinyl group, a quinolinyl group, an isoquinolinyl group, a quinolyl group, a phthalazinyl group, a naphthyridinyl group, a quinoxalinyl group, a quinazolinyl group, a cinnolinyl group, a pteridinyl group, a carbazolyl group, a carbolinyl group, a phenanthridinyl group, an acridinyl group, a perimidinyl group, a phenanthrolinyl group, a phenazinyl group, a phenothiazinyl group, a furazanyl group, a phenoxadinyl group, a thiazolyl group, an oxazolinyl group, a dibenzodioxinyl group, a triazolyl group, a benzoxazolyl group, a benzothiazolyl group, a benzimidazolyl group, and a benzotriazolyl group. More preferable are a pyridyl group, a pyrimidinyl group, a triazinyl group, and a carbazolyl group.

Preferable examples of the substituted amine groups include amine groups substituted by the aromatic hydrocarbon groups or aromatic heterocyclic groups cited above.

Preferable examples of the alkyl groups of 1 to 12 carbon atoms include a methyl group, an ethyl group, a propyl group, an isopropyl group, a butyl group, a sec-butyl group, a tert-butyl group, a pentyl group, a hexyl group, a heptyl group, an octyl group, and a stearyl group. Preferable examples of the alkoxyl groups of 1 to 12 carbon atoms include those alkoxyl groups which correspond to the aforementioned alkyl groups.

In the case where $R_1$ is an aromatic hydrocarbon group of 6 to 25 carbon atoms or aromatic heterocyclic group of 2 to 24 carbon atoms, the said aromatic hydrocarbon group or aromatic heterocyclic group may have a substituent. When such a substituent contains carbon atoms, the number of these carbon atoms in the substituent is included in the calculation of the total number of carbon atoms. When $R_1$ or $R_2$ is an amino group substituted by a hydrocarbon group or heterocyclic group, the said hydrocarbon group or heterocyclic group may have a substituent. Preferable examples of the substituents which the said aromatic hydrocarbon group, aromatic heterocyclic group, hydrocarbon group or heterocyclic group may have include aromatic hydrocarbon groups, alkyl groups of 1 to 12 carbon atoms, heterocyclic groups, and substituted amino groups.

Concrete examples of the aforementioned substituents include an alkyl group, an aurally group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an alkylsulfonyl group, a haloalkyl group, a hydroxyl group, an amide group, a substituted or unsubstituted aromatic hydrocarbon group, and a substituted or unsubstituted aromatic heterocyclic group. Preferable examples of the said substituents include an alkyl group of 1 to 4 carbon atoms, an alkoxyl group of 1 to 4 carbon atoms, a phenoxy group, a substituted amino group, a substituted or unsubstituted aromatic hydrocarbon group of 5 to 18 carbon atoms, and a substituted or unsubstituted aromatic heterocyclic group of 3 to 17 carbon atoms. More preferable examples include an aromatic hydrocarbon group of 6 to 14 carbon atoms and an aromatic heterocyclic group of 3 to 13 carbon atoms.

Although four $R_1$s in general formula (1) can change independently, they are preferably substituents other than hydrogen. Further, although two $R_2$s in general formula (1) can change independently, they are preferably hydrogen atoms or alkyl groups of 1 to 12 carbon atoms. More preferably, in general formula (1), four $R_1$s are phenyl groups or phenyl groups substituted by an alkyl group of 1 to 3 carbon atoms and two $R_2$s are hydrogen atoms or alkyl groups of 1 to 3 carbon atoms.

The compound having 2,2'-bipyrimidyl as a basic skeleton represented by general formula (1) has high triplet excitation energy as the two pyrimidine rings assume a distorted structure due to repulsion of the four nitrogen atoms at the 1-, 1'-, 3-, and 3'-positions. Further, this basic structure has a good electron injection/transport property and it is possible to maintain this electron injection/transport property and improve the hole injection/transport property by introduction of an aromatic hydrocarbon group, aromatic heterocyclic group, or substituted amino group to the basic structure. The aforementioned account explains how the compound of this invention has realized its well-balanced electrical charges injection/transport properties. In particular, introduction of an aromatic group or substituted amino group at the 4-, 4'-, 6-, and 6'-positions makes it possible to maintain the triplet excitation energy at a high level and control the injection/transport properties of holes and electrons.

Examples of the compounds represented by general formula (1) are shown below.

(1)
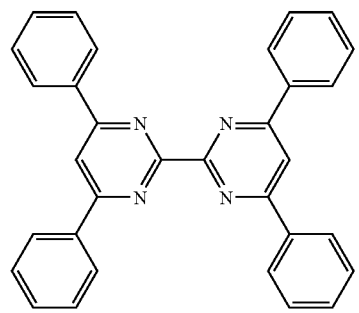
(2)
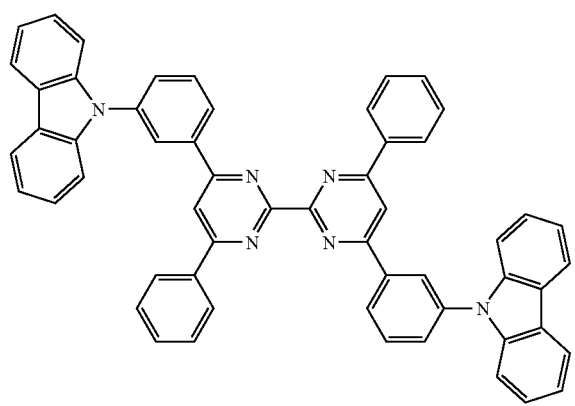
(3)
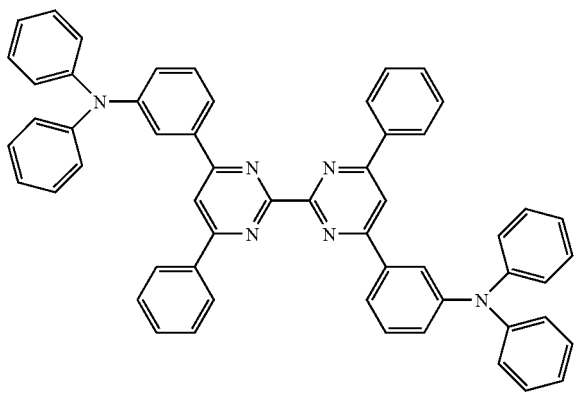
(4)
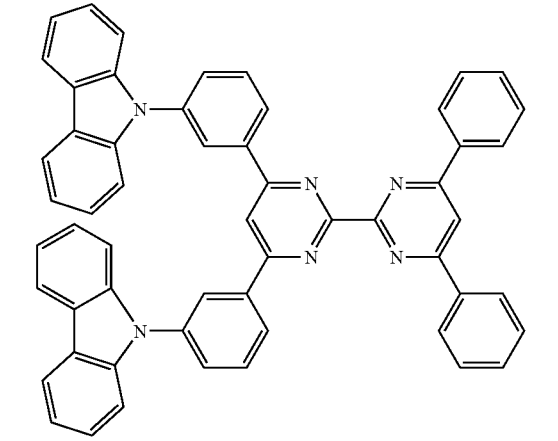
(5)
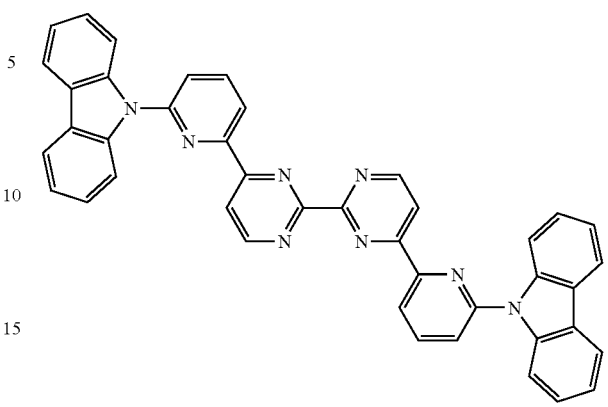
(6)
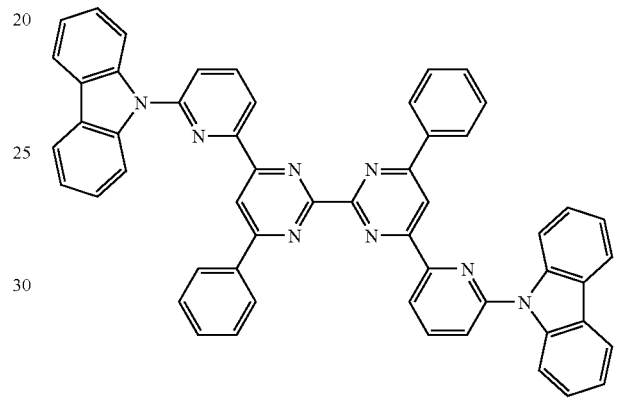
(7)
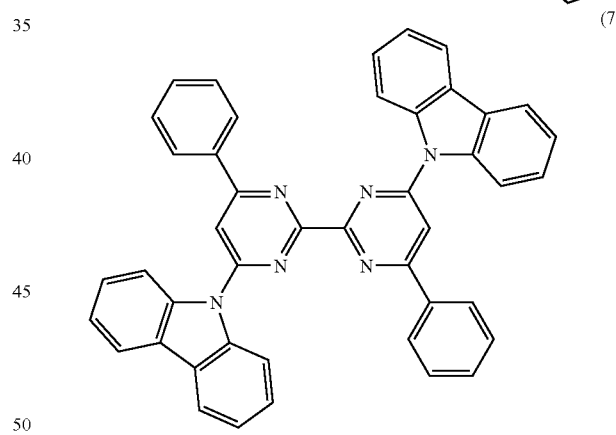
(8)
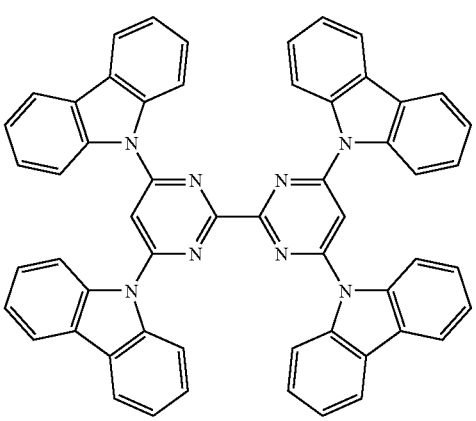

(9)
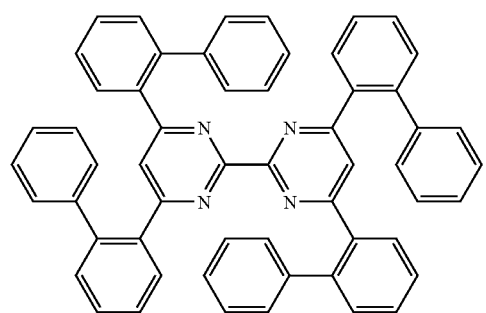
(10)
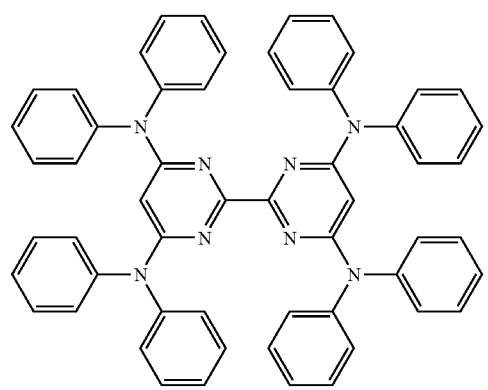
(11)
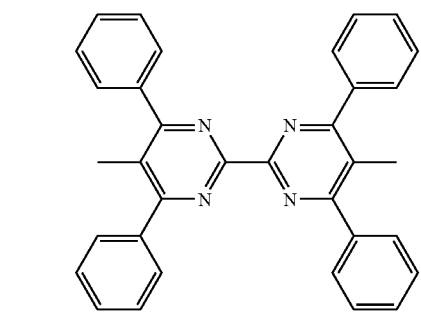
(12)
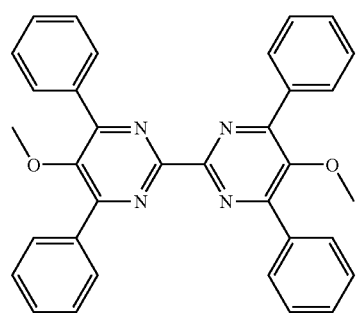
(13)
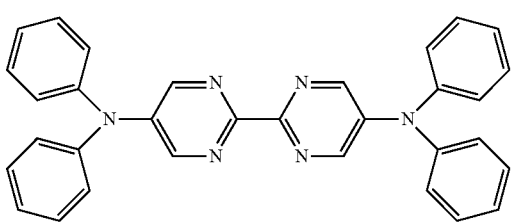
(14)
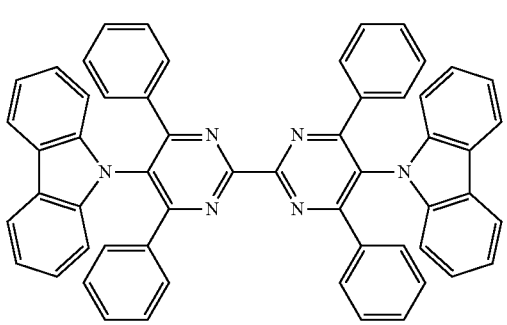
(15)
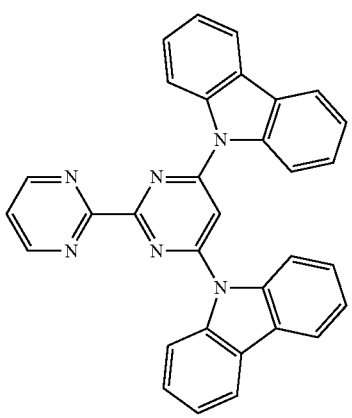
(16)
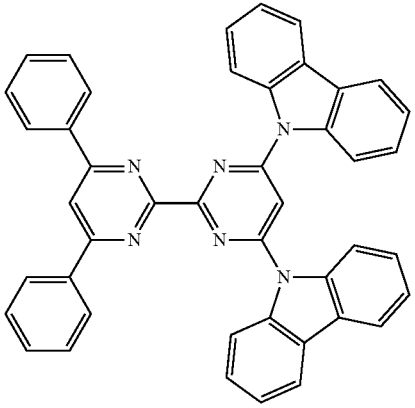
(17)
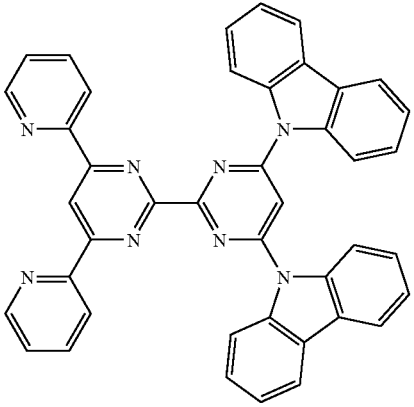

-continued
(18)
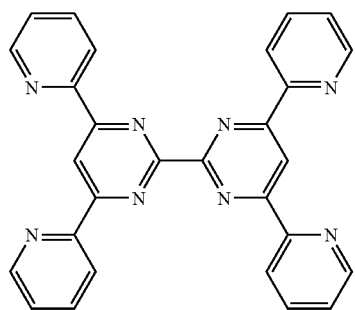
(22)
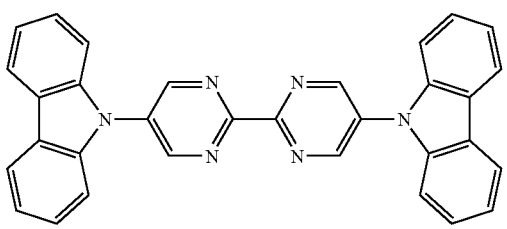
(19)
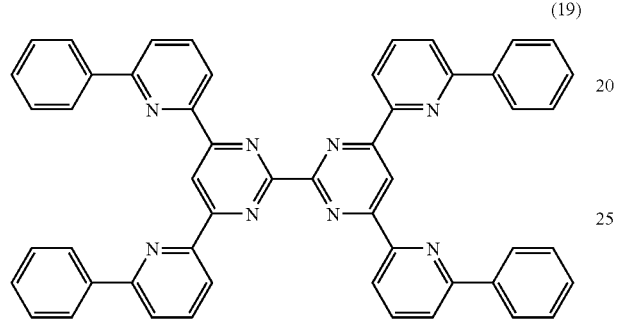
(23)
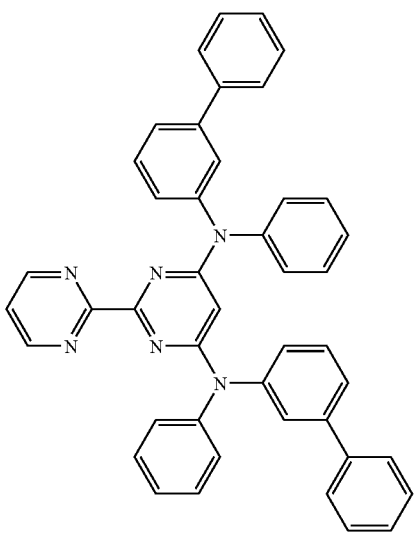
(20)
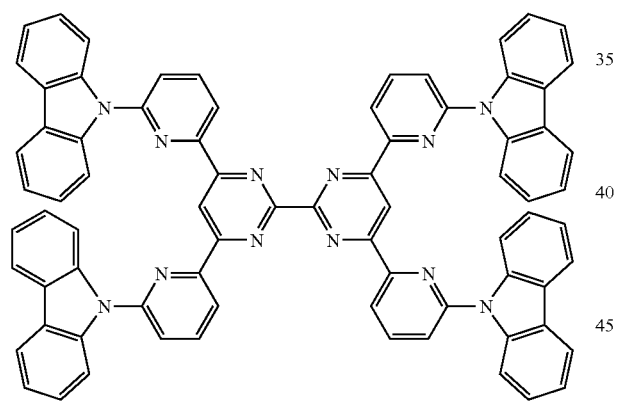
(24)
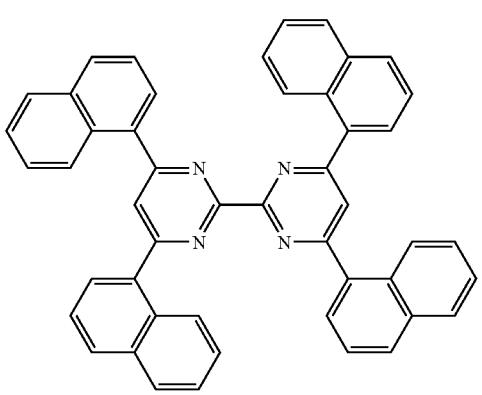
(21)
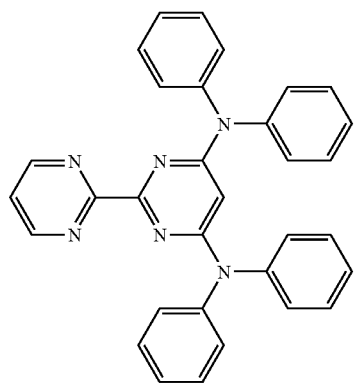
(25)
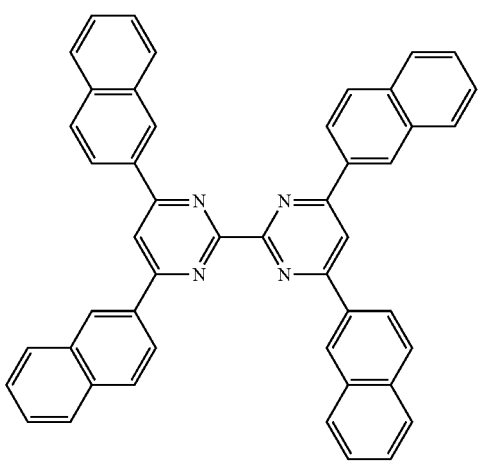

(26)
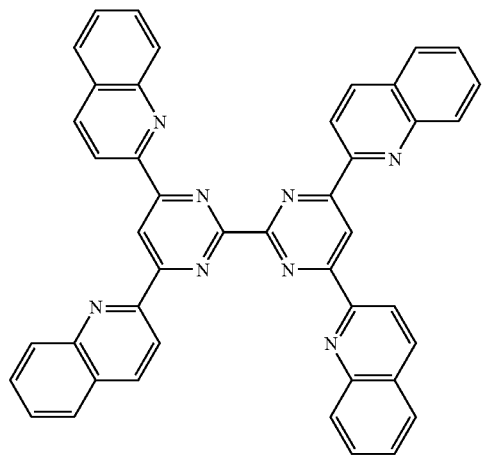
(29)
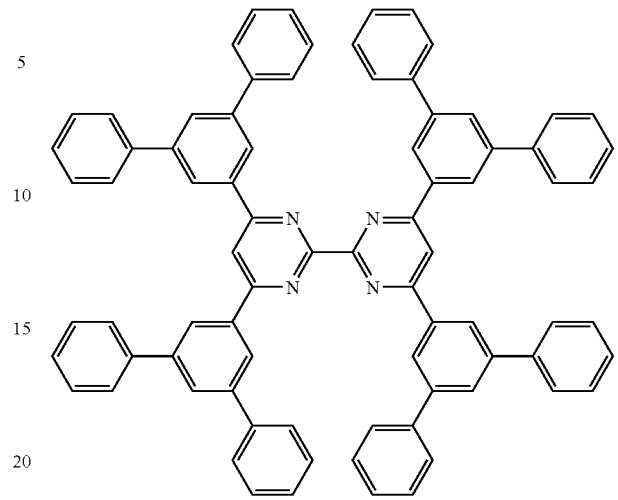
(27)
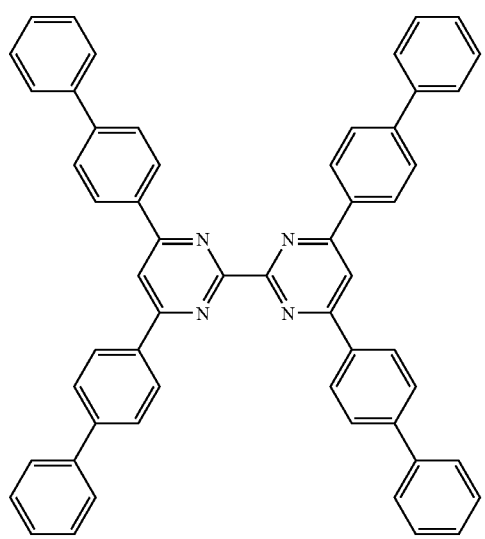
(30)
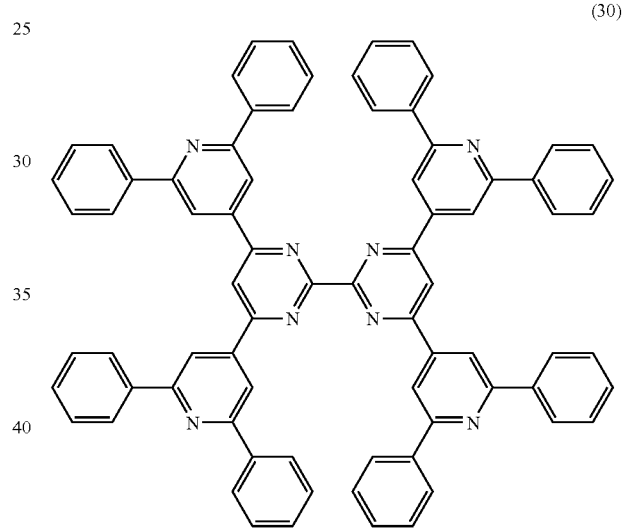
(28)
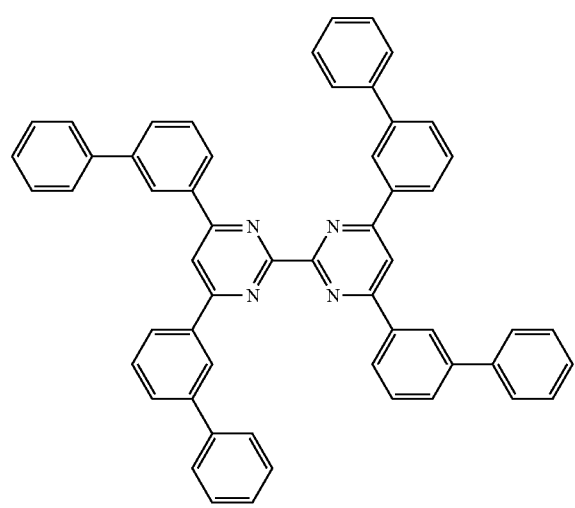
(31)
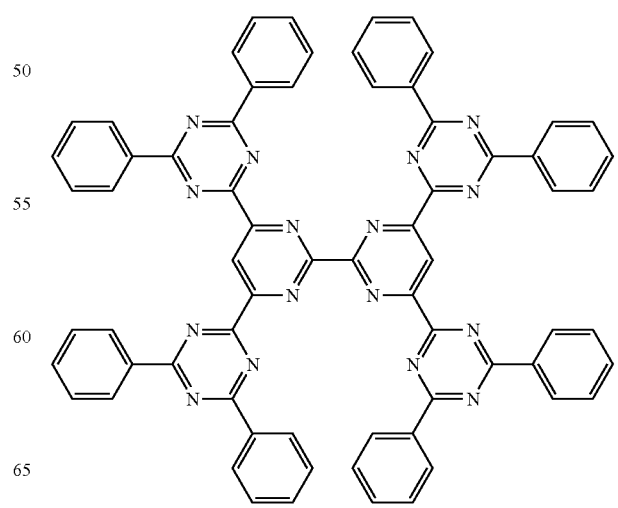

(32)
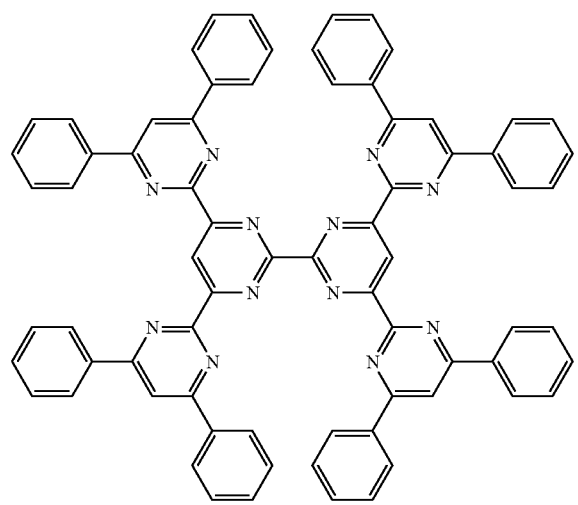
(33)
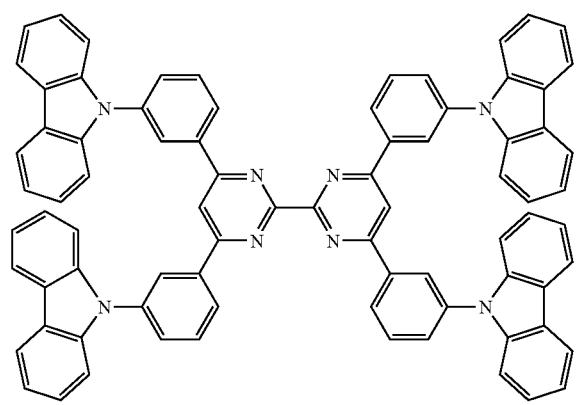
(34)
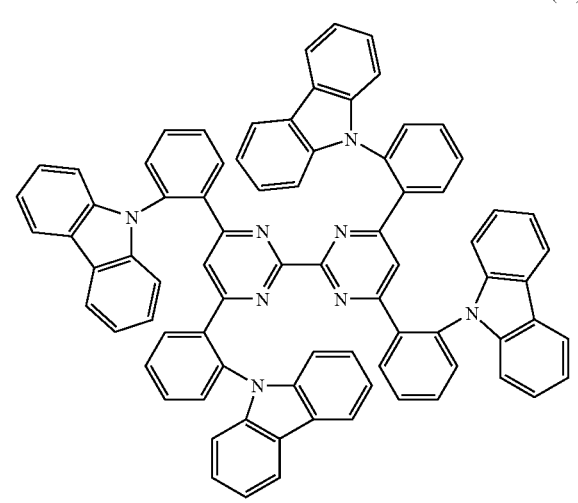
(35)
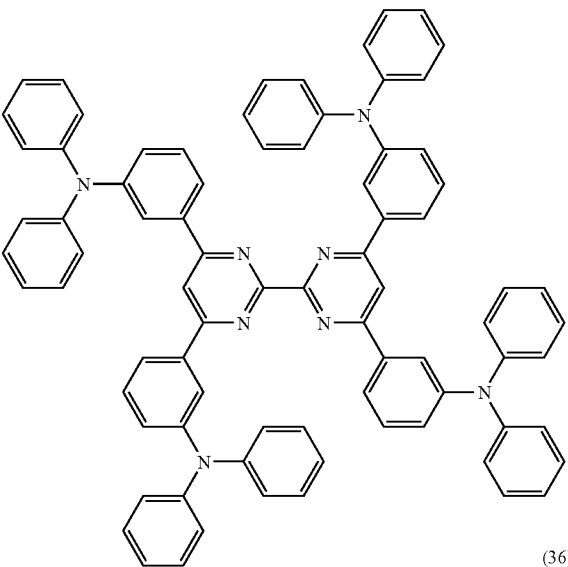
(36)
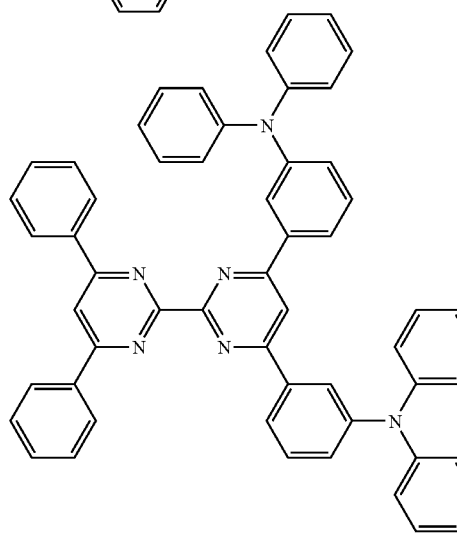
(37)
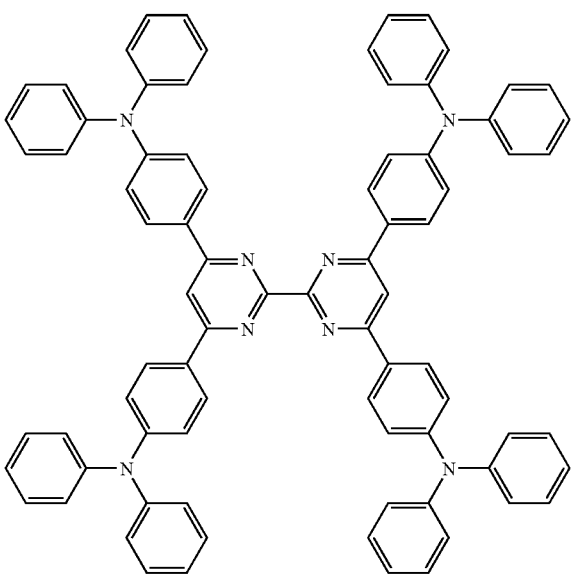

(38)

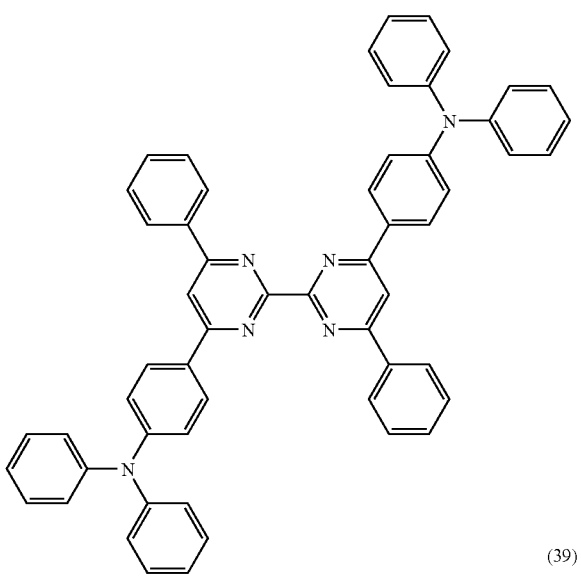

(39)

(40)

The compound for organic electroluminescent device of this invention is incorporated in the organic layer of an organic EL device to yield an excellent organic electroluminescent device. Preferably, the compound is incorporated in the light-emitting layer; more preferably, it is incorporated as a host material in the light-emitting layer containing a phosphorescent dopant.

Phosphorescent dopants to be used in the light-emitting layer are preferably organic metal complexes containing at least one metal selected from ruthenium, rhodium, palladium, silver, rhenium, osmium, iridium, platinum, and gold. Such organic metal complexes are known in the aforementioned patent documents and elsewhere and a suitable complex can be selected from them and used in this invention.

Preferable phosphorescent dopants include complexes having a noble metal element such as Ir in the center, typically Ir(ppy)3, complexes such as Ir(bt)2.acac3, and complexes such as PtOEt3. Examples of these complexes are shown below, but are not limited thereto.

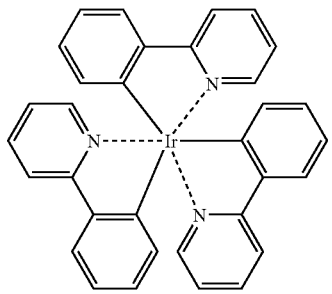

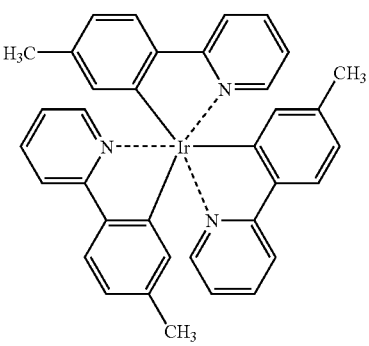

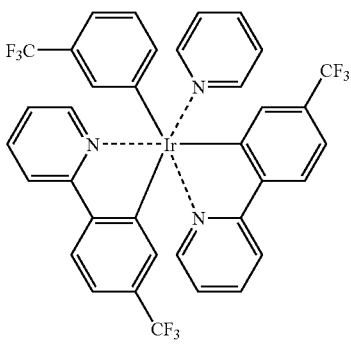

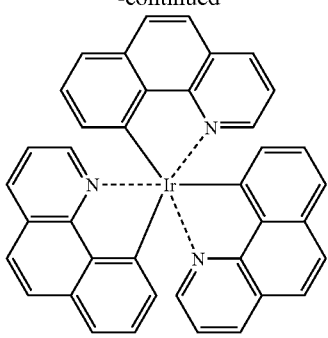
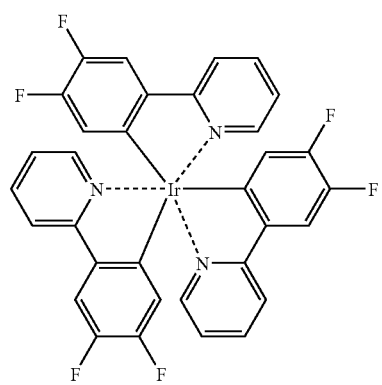
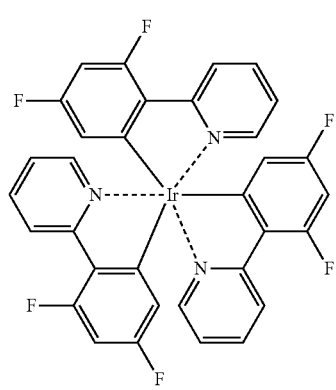
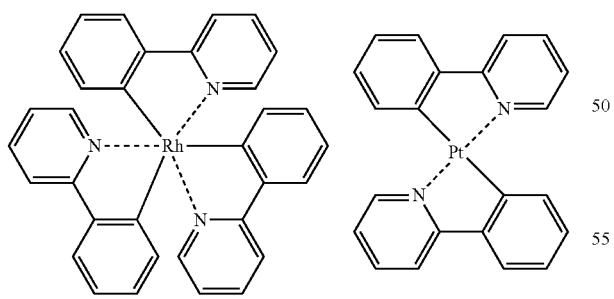
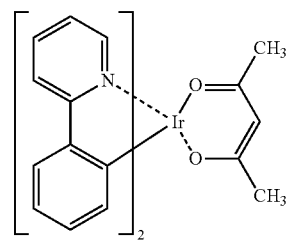
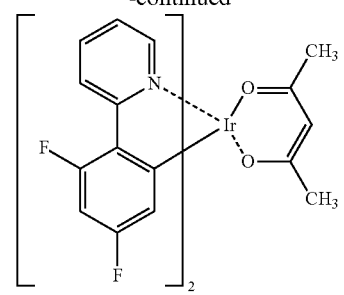
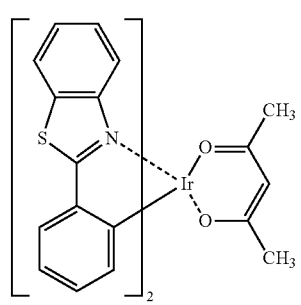
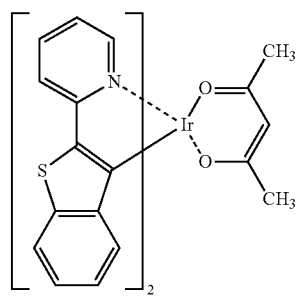
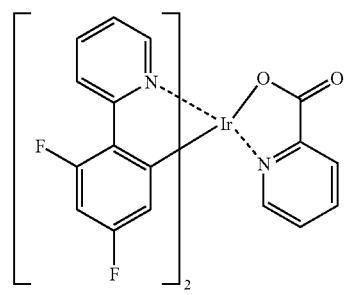
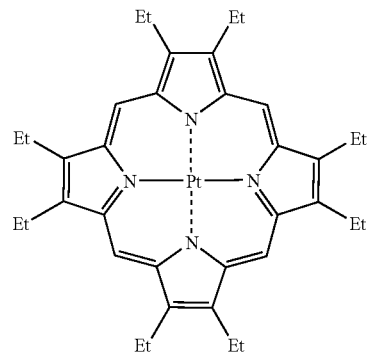

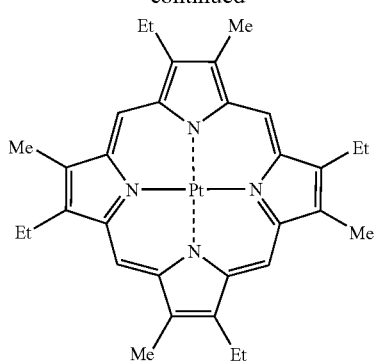

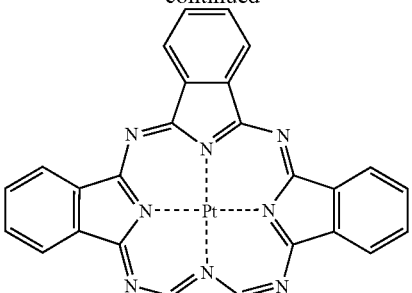

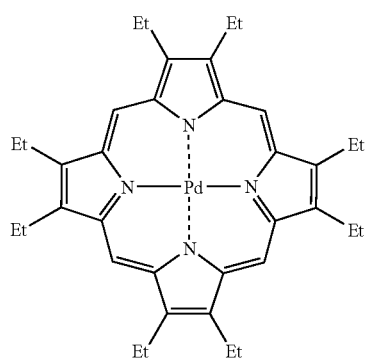

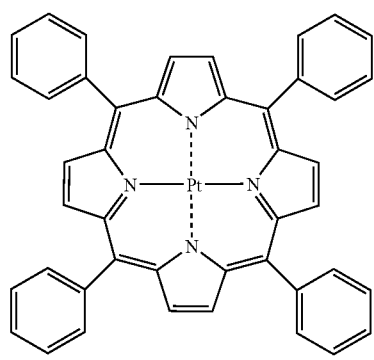

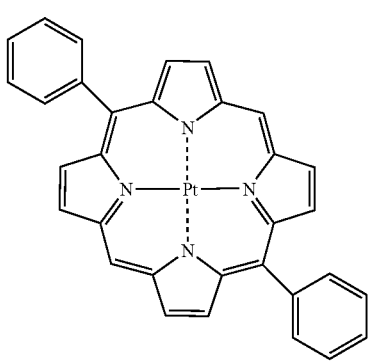

In the case where a phosphorescent dopant is incorporated in the light-emitting layer, the content of such a dopant is in the range of 1 to 20 wt %, preferably in the range of 5 to 10 wt %. In this case, the content of the compound for organic EL device of this invention represented by the aforementioned general formula (1) in the light-emitting layer is 50 wt % or more, preferably 70 wt % or more, more preferably in the range of 90 to 95 wt %. It is allowable to incorporate a host material other than the compound for organic EL device of this invention in the light-emitting layer. However, it is preferable that the compound for organic EL device of this invention accounts for 80 wt % or more or the whole of the host materials in use.

An organic device using the compound of this invention will be explained next.

The organic EL device of this invention has organic layers containing at least a light-emitting layer disposed between an anode and a cathode piled one upon another on a substrate and at least one of the organic layers contains the compound for organic EL device of this invention. Advantageously, the light-emitting layer contains the compound for organic EL device of this invention. More advantageously, the light-emitting layer contains a phosphorescent dopant together with the compound for organic EL device of this invention.

The structure of the organic EL device of this invention will be explained with reference to the drawing, but it will not be limited to the one shown in the drawing.

FIG. 1 schematically shows the structure of an example of an organic EL device generally used in this invention and the numbers in FIG. 1 respectively designate the following: 1 substrate, 2 anode, 3 hole-injecting layer, 4 hole-transporting layer, 5 light-emitting layer, 6 electron-transporting layer, and 7 cathode. The organic EL device of this invention contains a substrate, an anode, a light-emitting layer, and a cathode as essential layers; in addition to the essential layers, the device preferably has a hole-injecting/transporting layer and an electron-injecting/transporting layer and, further, a hole-blocking layer between the light-emitting layer and the electron-injecting/transporting layer. The term hole-injecting/transporting layer means a hole-injecting layer and/or a hole-transporting layer and the term electron-injecting/transporting layer means an electron-injecting layer and/or an electron-transporting layer.

It is possible to fabricate a device with a structure that is the reverse of the one shown in FIG. 1 by piling the cathode 7, the electron-transporting layer 6, the light-emitting layer 5, the hole-transporting layer 4, and the anode 2 one upon another in this order on the substrate 1 and, as described earlier, it is possible to dispose the organic EL device of this invention between two substrates at least one of which is highly transparent. In this case of the reverse structure, a layer or layers may be added or omitted as needed.

The organic EL device of this invention is applicable to a single device, a device with its structure arranged in array, or a device in which the anode and the cathode are arranged in X-Y matrix. The organic EL device of this invention produces remarkable improvements in luminous efficiency and driving stability over the conventional devices utilizing emission of light from the excited singlet state by incorporating a compound of specified skeleton and a phosphorescent dopant in its light-emitting layer and the device can perform excellently when applied to full-color or multicolor panels.

EXAMPLES

This invention will be described in more detail with reference to the examples; however, it will not be limited to these examples and it can be reduced to practice in various modes unless such practice exceeds the substance of this invention.

Example 1

Compound 1 was synthesized by the route shown below. The compound numbers correspond to those assigned to the compounds with chemical formulas cited earlier as examples.

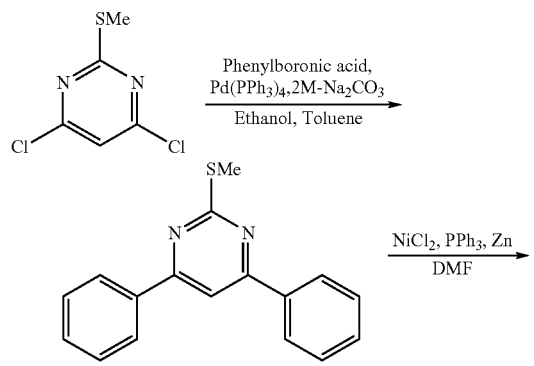

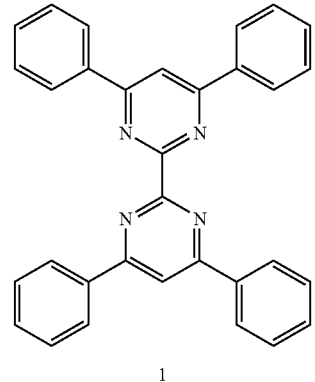

1

In a 2000-ml three-necked flask were placed 15.0 g (76.9 millimoles) of 4,6-dichloro-2-(methylthio)pyrimidine, 24.3 g (185 millimoles) of phenylboronic acid, 6.80 g (6.15 millimoles) of tetrakis(triphenylphosphine)palladium(0), 200 ml of ethanol, and 600 ml of toluene and stirred under flow of nitrogen. Then, 60.0 g of sodium carbonate was dissolved in 285 ml of water, the aqueous solution was added to the flask, and the mixture was stirred overnight at 90° C. The mixture in the flask was cooled to room temperature, 500 ml of water was added, and the resulting mixture was stirred and separated into an organic layer and an aqueous layer. The organic layer was washed three times with 200 ml of water and then dehydrated over magnesium sulfate, the magnesium sulfate was filtered off, and the solvent was distilled off under reduced pressure to give a gray solid (30.0 g). The gray solid was treated with activated carbon to give a white powder (25.0 g).

Then, 9.30 g (72 millimoles) of anhydrous nickel chloride, 75.5 g (288 millimoles) of triphenylphosphine, and 300 ml of dimethylformamide were added to a 2000-ml three-necked flask under nitrogen flow and the flask was deaerated for 15 minutes. The mixture was stirred at 50° C. for 15 minutes, 7.02 g (108 millimoles) of zinc was added to the flask, and the resulting mixture was stirred for 30 minutes. Thereafter, 20.0 g (72 millimoles) of the white powder obtained above was dissolved in 200 ml of dimethylformamide, the solution was added to the flask, and the mixture was stirred at 90° C. for three days. The mixture was cooled to room temperature, 500 ml of 10% ammonia water was added, the mixture was stirred, and a gray solid separated was collected by filtration. The solid was purified by crystallization from THF and methanol to give a light yellow solid. The solid was treated with activated carbon to give Compound 1 (4.95 g) as a white powder.

APCI-MS, m/z 463 [M+1]$^+$; melting point, 257° C.

Example 2

Applying the vacuum deposition process at a degree of vacuum of $4.0 \times 10^{-4}$ Pa, the constituent layers were respectively formed in thin film on a glass substrate having a 110 nm-thick indium tin oxide (ITO) anode formed hereon. First, copper phthalocyanine (CuPC) was deposited on the ITO anode to a thickness of 30 nm as a hole-injecting layer. Then, NPB was deposited to a thickness of 80 nm as a hole-transporting layer. Next, Compound 1 and iridium(III)bis(4,6-difluorophenyl)pyridinato-N,C2') picolinate (FIrpic), a blue phosphorescent emitter, were co-deposited from different evaporation sources to a thickness of 35 nm on the hole-transporting layer as a light-emitting layer. The concentration of Flrpic was 8.0%. Then, Alq3 was deposited to a thickness of 25 nm as an electron-transporting layer. Further, lithium fluoride (LiF) was deposited to a thickness of 0.5 nm on the electron-transporting layer as an electron-injecting layer. Finally, aluminum (Al) as an electrode was deposited to a thickness of 170 nm on the electron-injecting layer to complete the fabrication of an organic EL device. This device has a structure shown in FIG. 1 to which the electron-injecting layer is added between the cathode and the electron-transporting layer.

The organic EL device thus fabricated was connected to an outside power source and, upon application of direct current voltage, emission of light from the device with the characteristics shown in Table 1 was confirmed. The luminance, voltage, and luminous efficiency are measured at 10 mA/cm². The maximum wavelength of the spectrum of light emitted from the device is 470 nm and this proves that light is emitted from Flrpic.

Example 3

An organic EL device was fabricated as in Example 2 with the exception of using Compound 8 as a host material for the light-emitting layer. The luminous characteristics are shown in Table 1. The maximum wavelength of the spectrum of light emitted from the device is 470 nm and this proves that light is emitted from Flrpic.

Example 4

An organic EL device was fabricated as in Example 2 with the exception of using Compound 10 as a host material for the light-emitting layer. The luminous characteristics are shown in Table 1. The maximum wavelength of the spectrum of light emitted from the device is 470 nm and this proves that light is emitted from Flrpic.

Example 5

An organic EL device was fabricated as in Example 2 with the exception of using Compound 22 as a host material for the light-emitting layer. The luminous characteristics are shown in Table 1. The maximum wavelength of the spectrum of light emitted from the device is 470 nm and this proves that light is emitted from Flrpic.

Comparative Example 1

An organic EL device was fabricated as in Example 2 with the exception of using 1,3-dicarbazolylbenzene (mCP) as a host material for the light-emitting layer. The luminous characteristics are shown in Table 1.

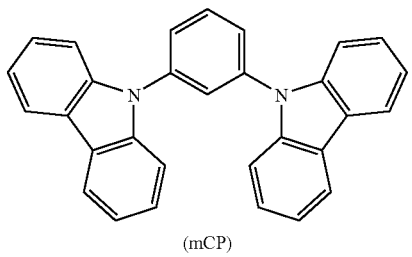 [SMILES: c1cc(-n2c3ccccc3c3ccccc32)cc(-n2c3ccccc3c3ccccc32)c1]
(mCP)

Comparative Example 2

An organic EL device was fabricated as in Example 2 with the exception of using H-1 as a host material for the light-emitting layer. The luminous characteristics are shown in Table 1.

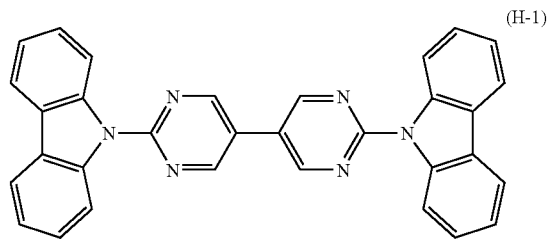 [SMILES: c1ccc2c(c1)c1ccccc1n2-c1ncc(-c2cnc(-n3c4ccccc4c4ccccc43)nc2)cn1]
(H-1)

Comparative Example 3

An organic EL device was fabricated as in Example 2 with the exception of using H-2 as a host material for the light-emitting layer. The luminous characteristics are shown in Table 1.

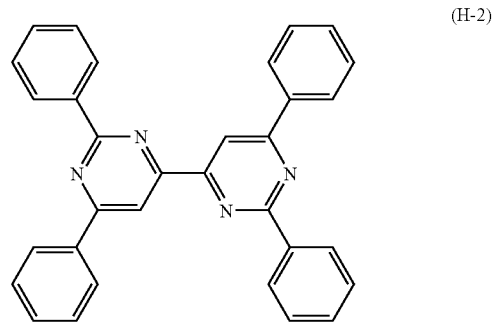 [SMILES: c1ccc(-c2cc(-c3cc(-c4ccccc4)nc(-c4ccccc4)n3)nc(-c3ccccc3)n2)cc1]
(H-2)

TABLE 1

|  | Luminance (cd/m²) | Voltage (V) | Luminous efficiency (lm/W) |
| --- | --- | --- | --- |
| Example 2 | 1140 | 9.8 | 3.7 |
| Example 3 | 1215 | 8.2 | 4.7 |
| Example 4 | 1145 | 9.7 | 3.7 |
| Example 5 | 950 | 9.9 | 3.0 |
| Comparative example 1 | 875 | 13.2 | 2.1 |
| Comparative example 2 | 210 | 9.6 | 0.7 |
| Comparative example 3 | 85 | 9.4 | 0.3 |

It is apparent from Table 1 that the luminous efficiency is higher in the examples in which the compound of this invention is used as a host material (Examples 2-5) than in the example in which mCP, a known blue emitter, is used as a host material (Comparative Example 1). Further, H-1 whose basic skeleton is 5,5'-bipyrimidyl (Comparative Example 2) or H-2 whose basic skeleton is 4,4'-bipyrimidyl (Comparative Example 3) shows low luminous efficiency and this proves the usefulness of 2,2'-bipyrimidyl as a basic skeleton.

The compound for organic EL device of this invention has good electrical charges injection/transport properties and its use in an organic EL device reduces the driving voltage of the device. Further, the compound balances electrical charges in the light-emitting layer well and improves the probability of recombination. Still further, the lowest triplet excitation energy of the compound is sufficiently high to confine the lowest triplet excitation energy of a dopant and, for this reason, the compound can effectively suppress transfer of the triplet excitation energy from the dopant to the host molecule. These features of the compound contributed to attain high luminous efficiency. In addition, the compound has a good property in the amorphous state, high heat resistance, and good electrochemical stability and realizes an organic EL device of long driving life and high durability.

INDUSTRIAL APPLICABILITY

The organic EL device of this invention is at a satisfactory level for practical use in respect to luminous efficiency, driving life, and durability and is technically highly valuable in applications to flat panel displays (cell phone display devices, vehicle display devices, office computer display devices, television sets, and the like), light sources utilizing the characteristics of planar light emitters (light sources for illumination and copying machines and backlight sources for liquid crystal displays and instruments), signboards, and beacon lights.

The invention claimed is:

1. An organic electroluminescent device constituted of an anode, one or multiple organic layers, and a cathode piled one upon another on a substrate wherein at least one of the organic layers is a light-emitting layer, the said light-emitting layer contains a host material and a phosphorescent dopant, and the host material contains a compound for organic electroluminescent device represented by the following general formula (1):

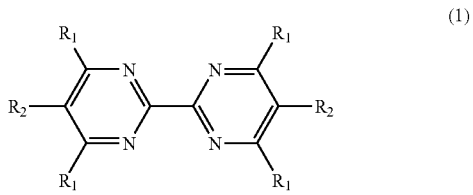

in the formula, $R_1$ is a phenyl group or a phenyl group substituted by an alkyl group of 1 to 3 carbon atoms and $R_2$ is a hydrogen atom or an alkyl group of 1 to 3 carbon atoms.

2. An organic electroluminescent device as described in claim 1 wherein the content of the phosphorescent dopant in the light-emitting layer is 5 to 10 wt %.

3. An organic electroluminescent device as described in claim 1 wherein, in formula (1), $R_1$ is a phenyl group or a phenyl group substituted by an alkyl group of 1 to 3 carbon atoms and $R_2$ is an alkyl group of 1 to 3 carbon atoms.

4. An organic electroluminescent device as described in claim 1, wherein the phosphorescent dopant in the light-emitting layer is an organic metal complex containing at least one metal selected from the group consisting of ruthenium, rhodium, palladium, silver, rhenium, osmium, iridium, platinum, and gold.

* * * * *